(12) United States Patent
Lysenko et al.

(10) Patent No.: US 8,124,812 B2
(45) Date of Patent: Feb. 28, 2012

(54) ALDEHYDE COMPOSITIONS DERIVED FROM SEED OILS

(75) Inventors: Zenon Lysenko, Midland, MI (US); Donald L. Morrison, Fort Collins, CO (US); David A. Babb, Lake Jackson, TX (US); Donald L. Bunning, South Charleston, WV (US); Christopher W. Derstine, Winfield, WV (US); James H. Gilchrist, Dunbar, WV (US); H. Ray Jouett, Houston, TX (US); Jeffrey S. Kanel, Hurricane, WV (US); Kurt D. Olson, Cross Lanes, WV (US); Wei-Jun Peng, Hurricane, WV (US); Joe D. Phillips, Lake Jackson, TX (US); Brian M. Roesch, Cross Lanes, WV (US); Aaron W. Sanders, Missouri City, TX (US); Alan K. Schrock, Lake Jackson, TX (US); Pulikkottil J. Thomas, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 12/565,446

(22) Filed: Sep. 23, 2009

(65) Prior Publication Data
US 2010/0298610 A1 Nov. 25, 2010

Related U.S. Application Data

(62) Division of application No. 10/551,854, filed as application No. PCT/US2004/012246 on Apr. 22, 2004, now Pat. No. 7,615,658.

(60) Provisional application No. 60/465,663, filed on Apr. 25, 2003.

(51) Int. Cl.
*C07C 47/02* (2006.01)
*C07C 45/50* (2006.01)
*C07C 29/14* (2006.01)
*C07C 59/147* (2006.01)

(52) U.S. Cl. ........ 568/448; 568/474; 568/882; 568/909; 554/120; 554/143

(58) Field of Classification Search .............. 554/1, 120, 554/143; 568/454, 455
See application file for complete search history.

(56) References Cited

U.S. PATENT DOCUMENTS 3,787,459 A  1/1974  Frankel
(Continued)

FOREIGN PATENT DOCUMENTS

BR  9503081  8/1996
(Continued)

OTHER PUBLICATIONS

"Producing Polyurethane Foam from Natural Oil," Catalysis of Organic Reactions, Aaron Sanders, et al., edited by Stephen R. Schmidt, CRC Press, New York, 2007, pp. 377-384.

*Primary Examiner* — Yate K Cutliff

(57) ABSTRACT

An aldehyde composition derived by hydroformylation of a transesterified seed oil and containing a mixture of formyl-substituted fatty acids or fatty acid esters having the following composition by weight: greater than about 10 to less than about 95 percent monoformyl, greater than about 1 to less than about 65 percent diformyl, and greater than about 0.1 to less than about 10 percent triformyl-substituted fatty acids or fatty acid esters, and having a diformyl to triformyl weight ratio of greater than about 5/1; preferably, greater than about 3 to less than about 20 percent saturates; and preferably, greater than about 1 to less than about 20 percent unsaturates.

17 Claims, 1 Drawing Sheet

U.S. PATENT DOCUMENTS

| | | | |
|---|---|---|---|
| 4,423,162 A | 12/1983 | Peerman et al. | |
| 4,633,021 A | 12/1986 | Hanes | |
| 4,723,047 A | 2/1988 | Bahrmann et al. | |
| 4,731,486 A * | 3/1988 | Abatjoglou et al. | 568/454 |
| 5,177,228 A | 1/1993 | Sato et al. | |
| 5,180,854 A | 1/1993 | Abatjoglou et al. | |
| 5,756,854 A | 5/1998 | Bahrmann et al. | |
| 2005/0070620 A1 | 3/2005 | Herrington et al. | |
| 2010/0048753 A1 | 2/2010 | Peng et al. | |

FOREIGN PATENT DOCUMENTS

| | | | |
|---|---|---|---|
| CA | 2162083 | * | 5/1996 |
| DE | 19908978 | | 9/2000 |
| EP | 0063944 | | 7/1985 |
| WO | WO01/12581 | | 2/2001 |
| WO | WO2004/096882 | | 11/2004 |
| WO | WO2004/096883 | | 11/2004 |
| WO | WO2008/073729 | | 6/2008 |

* cited by examiner

Lactol
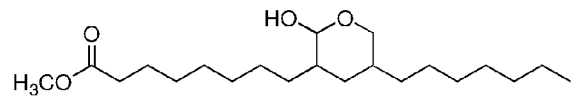
Lactone
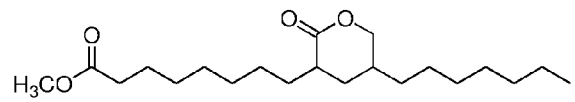
Saturated Cyclic Ether
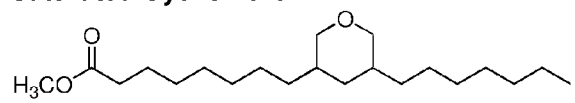
Unsaturated Cyclic Ether
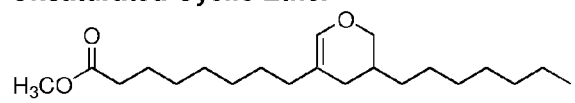
Dimer Heavies
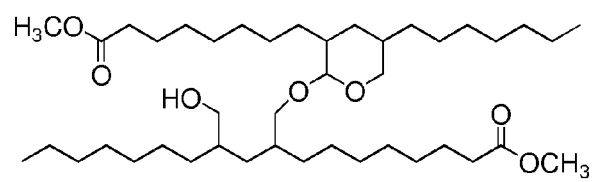
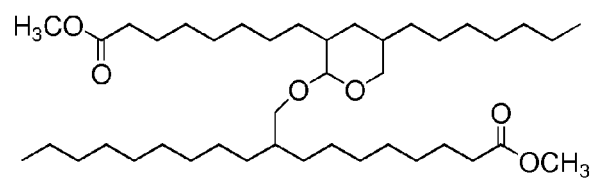
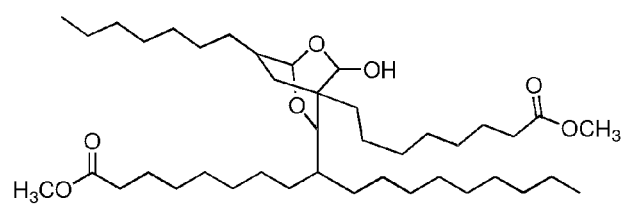
Condensation Heavies
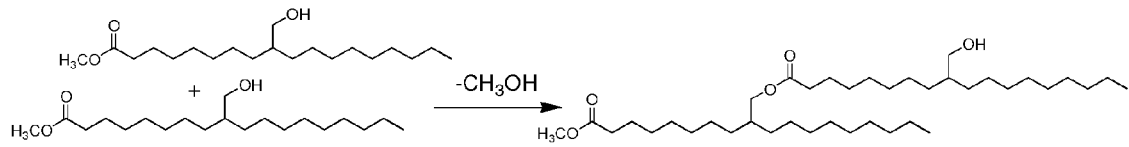

ALDEHYDE COMPOSITIONS DERIVED FROM SEED OILS

This application is divisional application of copending U.S. patent application Ser. No. 10/551,854, filed 30 Sep. 2005, which is a 371 continuation of International Application Serial No. PCT/US2004/012246 filed 22 Apr. 2004, which claims the benefits of Provisional Application Ser. No. 60/465,663, filed 25 Apr. 2003, the contents of these applications are herein incorporated by reference in their entirety

BACKGROUND OF THE INVENTION

In one aspect, this invention pertains to aldehyde and alcohol compositions, preferably, derived from seed oils. In another aspect, this invention pertains to a process of preparing the aldehyde composition via hydroformylation of an unsaturated fatty acid or unsaturated fatty acid ester feedstock derived from seed oils. Likewise, this invention also pertains to a process of preparing the alcohol composition via hydroformylation and subsequent hydrogenation of an unsaturated fatty acid or unsaturated fatty acid ester feedstock derived from seed oils.

Alcohol compositions are useful in that they can be converted into polyols that find utility in the manufacture of polyurethanes. Aldehyde compositions are useful in that they can be converted via hydrogenation into alcohols or amines, which in turn can be converted into polyols and polyamines for the manufacture of polyurethanes. Aldehydes can also be converted into carboxylic acids, hydroxy acids, amino alcohols, amino acids, and other commercially useful derivatives.

Currently, industry-wide efforts are underway to replace petroleum-based chemical feedstocks with non-petroleum-based chemical feedstocks. Seed oils, which comprise a mixture of saturated and unsaturated fatty acid esters, provide a promising source of renewable non-petroleum-based feedstocks for industrial utilization. Aldehydes and alcohols derived from seed oils have the potential to be converted into many useful industrial chemicals, notably, polyols for use in polyurethanes.

To be useful in polyurethane manufacture non-petroleum-based polyols should provide for similar reactivity and urethane end-product at acceptable cost, as compared with conventional petroleum-based polyols. Non-petroleum-based polyols may also provide opportunities for preparing unconventional polyurethane products having novel properties. The properties of polyurethanes are known to vary depending upon the polyol composition employed during polyurethane manufacture. Non-petroleum-based aldehyde and alcohol compositions should be engineered such that the polyols derived therefrom yield polyurethanes of acceptable properties for their desired end-use. Polyols to be used in manufacture of polyurethane slab stock flexible foams, for example, should provide for acceptable cross-link density, that is, cross-link density neither too high nor too low; else the foam has unacceptable rigidity or flexibility. The invention described herein pertains particularly to aldehyde and alcohol compositions that are preferably derived from seed oils and that provide for polyols having acceptable properties for the manufacture of polyurethane slab stock flexible foams.

Prior art, as exemplified by U.S. Pat. No. 3,787,459, discloses a process for converting unsaturated vegetable oil materials via hydroformylation into formyl(aldehyde) products. Disclosed vegetable oils include soybean, linseed, and safflower oils, and their derivatives. Typically, the process appears to be operated to conversions of greater than 90 percent total unsaturates. As best as can be determined, the formyl composition disclosed in U.S. Pat. No. 3,787,459 consists of from 24 to 92 percent monoformyl and from 17 to 75 percent diformyl products.

Other prior art, such as EP-B1-711748, discloses a process for preparing di- and polyformylcarboxylic esters by hydroformylation of esters of multiply unsaturated fatty acids, such as soybean oil, sunflower oil, linseed oil, and other vegetable oils. The conversion of feedstock appears to range from roughly 55 to 100 percent by weight. The resulting aldehyde composition, as illustrated in the examples, appears to comprise from 23 to 35 percent monoformyl, from 12 to 31 percent diformyl, and from 3 to 29 percent triformyl products, by weight.

Yet other prior art, illustrated by U.S. Pat. No. 5,177,228, discloses the hydroformylation of an unsaturated fatty acid ester, such as methyl oleate, to a monoformyl fatty acid ester, such as methylformyl stearate.

In view of the above, it would be advantageous to discover aldehyde and alcohol compositions that can be derived from renewable non-petroleum-based feedstocks, such as seed oils. Moreover, it would be advantageous to discover such aldehyde and alcohol compositions that can also be converted into polyols having acceptable properties for use in polyurethane slab stock flexible foam applications.

SUMMARY OF THE INVENTION

In a first aspect, this invention provides for a novel aldehyde composition comprising a mixture of formyl-substituted fatty acids or fatty acid esters, which comprises in terms of formyl distribution from greater than about 10 to less than about 95 percent monoformyl, from greater than about 1 to less than about 65 percent diformyl, and from greater than about 0.1 to less than 10 percent triformyl by weight, based on the total weight of the composition. In addition, the aldehyde composition of this invention is characterized by a diformyl to triformyl weight ratio of greater than about 5/1.

The novel aldehyde composition of this invention can be hydrogenated or aminated to the corresponding alcohol or amine, which is a useful starting material for the preparation of polyols or polyamines, respectively. Polyols and polyamines find utility in the preparation of polyurethane slab stock flexible foams and other polyurethane products. The aldehyde composition of this invention can also be converted into other industrially useful chemicals, including carboxylic acids, hydroxyacids, and amino acids. Advantageously, the aldehyde and alcohol compositions of this invention can be derived from seed oils, which provide for a renewable non-petroleum based raw material feedstock.

In a second aspect, this invention provides for a process of preparing the novel aldehyde composition described hereinabove, comprising contacting a mixture of unsaturated fatty acids or fatty acid esters with carbon monoxide and hydrogen in the presence of a Group VIII transition metal-organophosphine metal salt ligand complex catalyst, and optionally free organophosphine metal salt ligand, under process conditions sufficient to convert greater than about 80 weight percent of the unsaturated fatty acids or fatty acid esters to monoformyl product. (Measurement of conversion is explained in greater detail hereinafter.) In such a manner, a product mixture is obtained of formyl-substituted fatty acids or fatty acid esters comprising in terms of formyl distribution from greater than about 10 to less than about 95 percent monoformyl, from greater than about 1 to less than about 65 percent diformyl, and from greater than about 0.1 to less than 10 percent triformyl products by weight, based on the total weight of the composition. Additionally, the aldehyde composition is characterized by a diformyl to triformyl weight ratio of greater than about 5/1.

In a third aspect, this invention provides for a novel alcohol composition comprising a mixture of hydroxymethyl-substituted fatty acids or fatty acid esters, which comprises in terms of hydroxy distribution from greater than about 10 to less than about 95 percent monoalcohol {that is, mono(hydroxymethyl)}, from greater than about 1 to less than about 65 percent diol {that is, di(hydroxymethyl)}, and from greater than about 0.1 to less than about 10 percent triol {that is, tri (hydroxymethyl)} by weight, based on the total weight of the composition. The novel alcohol composition of this invention, advantageously derived from renewable non-petroleum-based seed oil feedstocks, can be used as a starting material for the preparation of polyols, which find utility in the preparation of polyurethane slab stock flexible foams and other polyurethane products.

In a fourth aspect, this invention provides for a process of preparing the novel alcohol composition described hereinabove, comprising (a) contacting a mixture comprising unsaturated fatty acids or fatty acid esters with carbon monoxide and hydrogen in the presence of Group VIII transition metal-organophosphine metal salt ligand complex catalyst, and optionally free organophosphine metal salt ligand, under conditions sufficient to hydroformylate greater than about 80 weight percent of unsaturated fatty acids or fatty acid esters to monoformyl product, thereby producing a hydroformylation reaction mixture comprising an aldehyde product of formyl-substituted fatty acids or fatty acid esters; (b) separating the aldehyde product from the hydroformylation reaction mixture; and thereafter (c) hydrogenating the aldehyde product with a source of hydrogen in the presence of a hydrogenation catalyst under process conditions sufficient to obtain the alcohol composition comprising a mixture of hydroxymethyl-substituted fatty acids or fatty acid esters, comprising in terms of hydroxy distribution from greater than about 10 to less than about 95 percent monoalcohol, from greater than about 1 to less than about 65 percent diol, and from greater than about 0.1 to less than about 10 percent triol, by weight, based on the total weight of the composition.

DRAWING

FIG. 1 illustrates a variety of impurity compounds that may be found in the alcohol composition, including a lactol, a lactone, a saturated cyclic ether, an unsaturated cyclic ether, dimer heavies, and condensation heavies.

DETAILED DESCRIPTION OF THE INVENTION

The inventions described herein allow for beneficial exploitation of naturally occurring and genetically modified seed oils in the preparation of renewable non-petroleum-based chemical feedstocks for use in manufacture of industrial chemicals, preferably, polyurethanes. In a first aspect related thereto, this invention provides for a novel aldehyde composition comprising a mixture of formyl-substituted fatty acids or fatty acid esters comprising in terms of formyl distribution from greater than about 10, preferably greater than about 25, to less than about 95 percent monoformyl, from greater than about 1 to less than about 65 percent diformyl, and from greater than about 0.1 to less than about 10 percent triformyl by weight, based on the total weight of the composition. The aldehyde composition is further characterized as comprising a diformyl to triformyl weight ratio of greater than about 5/1. For the purposes of this invention, the term "monoformyl" refers to any fatty acid or fatty acid ester having one formyl (—CHO) substituent. The formyl substituent may occur at any location along the fatty acid chain, which may be fully saturated or may contain one or more unsaturated double bonds. Analogously, the terms "diformyl" and "triformyl" will refer to any fatty acid or fatty acid ester having two or three formyl substituents, respectively, located at any site along the fatty acid chain. Likewise, the diformyl and triformyl substituted fatty acid or fatty acid ester may be saturated or unsaturated.

In a preferred embodiment, the aldehyde composition comprises greater than about 25 percent, more preferably, greater than about 30 percent monoformyl-substituted fatty acid(s) or fatty acid ester(s) by weight. In a preferred embodiment, the aldehyde composition comprises less than about 45 percent, and more preferably, less than about 40 percent monoformyl-substituted fatty acid(s) or fatty acid ester(s), by weight. In another preferred embodiment, the aldehyde composition comprises greater than about 20 percent, more preferably, greater than about 25 percent diformyl-substituted fatty acid(s) or fatty acid ester(s), by weight. In another preferred embodiment, the aldehyde composition comprises less than about 50 percent, more preferably, less than about 45 percent diformyl-substituted fatty acid(s) or fatty acid ester(s), by weight. In yet another preferred embodiment, the aldehyde composition comprises greater than about 0.5 percent, more preferably, greater than about 1 percent triformyl-substituted fatty acid(s) or fatty acid ester(s), by weight. In another embodiment, the aldehyde composition comprises less than about 5 percent, preferably less than about 4 percent, triformyl-substituted fatty acid(s) or fatty acid ester(s), by weight. In another embodiment, the aldehyde composition comprises less than about 2.6 percent triformyl-substituted fatty acid(s) or fatty acid ester(s), by weight. In another embodiment, the aldehyde composition comprises less than about 2.4 percent triformyl-substituted fatty acid(s) or fatty acid ester(s), by weight.

In a preferred embodiment, the aldehyde composition is characterized by a diformyl to triformyl weight ratio greater than about 8/1, more preferably, greater than about 10/1.

In a more preferred embodiment, the aldehyde composition comprises greater than about 3 percent saturates, even more preferably, greater than about 10 percent saturates, and most preferably, greater than about 12 percent saturates. In a more preferred embodiment, the aldehyde composition comprises less than about 20 percent saturates. For the purposes of this invention, the term "saturates" includes any fatty acid or fatty acid ester wherein each carbon atom in the fatty acid chain is covalently bonded to four elements (that is, no carbon-carbon double or triple bonds present), with the added requirement that the saturates will not contain any formyl or hydroxy substituents (other than those that might occur in the natural seed oil).

In another more preferred embodiment, the aldehyde composition comprises greater than about 1 percent unsaturates. In another more preferred embodiment, the aldehyde composition comprises less than about 20 percent unsaturates. For the purposes of this invention, the term "unsaturates" refers to any fatty acid or fatty acid ester that contains at least one carbon-carbon double bond, with the added requirement that such compounds will not contain any formyl or hydroxymethyl substituents (other than those that might occur in the natural seed oil).

In yet another preferred embodiment, the aldehyde composition comprises less than about 10 weight percent impurities, for example heavies, as described hereinafter.

In a second aspect, this invention provides for a process of preparing the novel aldehyde composition described hereinabove, comprising contacting a mixture of unsaturated fatty acids or fatty acid esters with carbon monoxide and hydrogen in the presence of a Group VIII transition metal-organophosphine metal salt ligand complex catalyst, and optionally free organophosphine metal salt ligand, under process conditions sufficient to hydroformylate, typically, greater than about 80 weight percent, and preferably, greater than about 80 weight percent and less than about 99 weight percent, of unsaturated fatty acids or fatty acid esters to monoformyl products, so as to obtain a mixture of formyl-substituted fatty acids or fatty acid esters comprising in terms of formyl distribution from greater than about 10 to less than about 95 percent monoformyl, from greater than about 1 to less than about 65 percent diformyl, and from greater than about 0.1 to less than about 10 percent triformyl by weight, based on the total weight of the aldehyde composition, and also having a diformyl to triformyl weight ratio greater than about 5/1.

In a third aspect, this invention provides for a novel alcohol composition comprising a mixture of hydroxymethyl-substituted fatty acids or fatty acid esters comprising in terms of hydroxy distribution from greater than about 10, preferably greater than about 25, to less than about 95 percent monoalcohol, {that is, mono(hydroxymethyl)}, from greater than about 1 to less than about 65 percent diol {that is, di(hydroxymethyl)}, and from greater than about 0.1 to less than about 10 percent triol {that is, tri(hydroxymethyl)}, by weight, based on the total weight of the composition. In U.S. Provisional Patent Application Ser. No. 60/465,663, filed Apr. 25, 2003, which is the priority document for the instant application, the term "hydroxy-substituted" is used, rather than the term "hydroxymethyl-substituted." One skilled in the art will recognize that in both the priority application and the instant application, the process invention involves the hydrogenation of a formyl group to a product alcohol. While the nomenclature of the priority application embraced the intended alcohol products, a more accurate nomenclature is reflected herein in use of the term "hydroxymethyl-substituted."

In a preferred embodiment, the alcohol composition comprises greater than about 25 percent, more preferably, greater than about 30 percent mono(hydroxymethyl)-substituted fatty acid(s) or fatty acid ester(s) (monoalcohol), by weight. In a preferred embodiment, the alcohol composition comprises less than about 70 percent, more preferably, less than about 45 percent, and most preferably, less than about 40 percent, mono(hydroxymethy)-substituted fatty acid(s) or fatty acid ester(s), by weight. In a preferred embodiment, the alcohol composition comprises greater than about 20 percent, and more preferably, greater than about 25 percent di(hydroxymethyl)-substituted fatty acid(s) or fatty acid ester(s) (diol), by weight. In a preferred embodiment, the alcohol composition comprises less than about 50 percent, and more preferably, less than about 45 percent di(hydroxymethyl)-substituted fatty acid(s) or fatty acid ester(s), by weight. In a preferred embodiment, the alcohol composition comprises greater than about 0.5 percent, and more preferably, greater than about 1 percent tri(hydroxymethyl)-substituted fatty acid(s) or fatty acid ester(s) (triol), by weight. In a preferred embodiment, the alcohol composition comprises less than about 5 percent, and more preferably, less than about 4 percent tri(hydroxymethyl)-substituted fatty acid(s) or fatty acid ester(s), by weight. The terms "monoalcohol," "diol," and "triol" may be used herein to refer to fatty acids or fatty acid esters having one, two, or three hydroxymethyl substituents, respectively, at any location along the fatty acid chain. The monoalcohols, diols, and triols may also be saturated or unsaturated.

In a more preferred embodiment, the alcohol composition comprises greater than about 3 percent, even more preferably, greater than about 10 percent, and most preferably, greater than about 15 percent saturates by weight. In a more preferred embodiment, the alcohol composition comprises less than about 35 percent, and most preferably, less than about 30 percent saturates by weight. The term "saturates" is given the same meaning as set forth hereinabove, which includes any fatty acid or fatty acid ester wherein each carbon atom in the fatty acid chain is covalently bonded to four elements (that is, no carbon-carbon double or triple bonds present), with the added requirement that the saturates do not contain any formyl or hydroxymethyl substituents (except as might occur naturally in the seed oil).

In another more preferred embodiment, the alcohol composition comprises less than about 10 percent unsaturates, by weight. The term "unsaturates" will have the same meaning as set forth hereinabove in reference to any fatty acid or fatty acid ester that contains at least one carbon-carbon double bond, with the added requirement that such components do not contain any formyl or hydroxymethyl substituents (except as may occur in the natural seed oil).

In yet another preferred embodiment, the alcohol composition is characterized by a diol to triol weight ratio of greater than about 2.5/1, more preferably greater than about 5/1, even more preferably, greater than about 8/1, and most preferably, greater than about 10/1.

In yet another preferred embodiment, the alcohol composition comprises less than about 10 weight percent impurities, including lactols, lactones, saturated and unsaturated cyclic ethers, and heavies, as described hereinafter.

In a fourth aspect, this invention provides for a process of preparing the novel alcohol composition described hereinabove, comprising (a) contacting a mixture comprising unsaturated fatty acids or fatty acid esters with carbon monoxide and hydrogen in the presence of a Group VIII transition metal-organophosphine metal salt ligand complex catalyst, and optionally, free organophosphine metal salt ligand, under conditions sufficient to hydroformylate typically greater than about 80 weight percent, and preferably greater than about 80 weight percent and less than about 99 weight percent, unsaturated fatty acids or fatty acid esters to monoformyl products, so as to obtain a hydroformylation reaction mixture comprising an aldehyde product of formyl-substituted fatty acids or fatty acid esters; (b) separating the aldehyde product from the hydroformylation reaction mixture; and thereafter (c) hydrogenating the aldehyde product with a source of hydrogen in the presence of a hydrogenation catalyst under process conditions sufficient to obtain the alcohol composition comprising a mixture of hydroxymethyl-substituted fatty acids or fatty acid esters comprising in terms of hydroxy distribution from greater than about 10 to less than about 95 percent monoalcohol, from greater than about 1 to less than about 65 percent diol, and from greater than about 0.1 to less than about 10 percent triol by weight, based on the total weight of the composition.

The fatty acid or fatty acid ester feedstock suitably employed in preparing the aldehyde and alcohol compositions of this invention is preferably derived from natural and genetically modified (GMO) plant and vegetable seed oils. Suitable non-limiting examples of such seed oils include castor, soybean, olive, peanut, rapeseed, corn, sesame, cottonseed, canola, safflower, linseed, sunflower; high oleic oils; genetically-modified variations of the aforementioned oils; as well as mixtures thereof. Preferably, the fatty acid or fatty acid ester feedstock is derived from soybean (natural and GMO), sunflower (including high oleic), and canola (including high oleic) oils. More preferably, the fatty acid or fatty acid ester feedstock is derived from natural or genetically modified soybean oils.

Typically, each fatty acid component of the seed oil comprises a fatty acid chain of greater than about 5, preferably, greater than about 10, and more preferably, greater than about 12 carbon atoms. Typically, the fatty acid chain contains less than about 50, preferably, less than about 35, and more preferably, less than about 25 carbon atoms. The fatty acid chain may be straight or branched and substituted with one or more substituents, provided that the substituents do not materially interfere with processes described herein and any desired downstream end-use. Non-limiting examples of suitable substituents include alkyl moieties, preferably $C_{1-10}$ alkyl moieties, for example methyl, ethyl, propyl, and butyl; cycloalkyl moieties, preferably, $C_{4-8}$ cycloalkyl; phenyl; benzyl; $C_{7-16}$ alkaryl and aralkyl moieties; hydroxy, ether, keto, and halide (preferably, chloro and bromo) substituents.

Seed oils comprise a mixture of both saturated and unsaturated fatty acids and/or fatty acid esters. For use in this invention, typically, the seed oil comprises greater than about 65 percent, preferably, greater than about 70 percent, and more preferably, greater than about 80 percent unsaturated fatty acids or fatty acid esters. For use in this invention, typically, the seed oil comprises from greater than about 20 to less than about 90 percent mono-unsaturated fatty acids or fatty acid esters; from greater than about 4 to less than about 56 percent di-unsaturated fatty acids or fatty acid esters; and from greater than about 1 to less than about 10 percent tri-unsaturated fatty acids or fatty acid esters, by weight. In seed oils the alcohol segment of the fatty acid ester is glycerol, a trihydric alcohol.

Non-limiting examples of suitable unsaturated fatty acids that may be found in the seed oil feedstock include 3-hexenoic (hydrosorbic), trans-2-heptenoic, 2-octenoic, 2-nonenoic, cis- and trans-4-decenoic, 9-decenoic (caproleic), 10-undecenoic (undecylenic), trans-3-dodecenoic (linderic), tridecenoic, cis-9-tetradeceonic (myristoleic), pentadecenoic, cis-9-hexadecenoic (cis-9-palmitoelic), trans-9-hexadecenoic (trans-9-palmitoleic), 9-heptadecenoic, cis-6-octadecenoic (petroselinic), trans-6-octadecenoic (petroselaidic), cis-9-octadecenoic (oleic), trans-9-octadecenoic (elaidic), cis-11-octadecenoic, trans-11-octadecenoic (vaccenic), cis-5-eicosenoic, cis-9-eicosenoic (godoleic), cis-11-docosenoic (cetoleic), cis-13-docosenoic (erucic), trans-13-docosenoic (brassidic), cis-15-tetracosenoic (selacholeic), cis-17-hexacosenoic (ximenic), and cis-21-triacontenoic (lumequeic) acids, as well as 2,4-hexadienoic (sorbic), cis-9-cis-12-octadecadienoic (linoleic), cis-9-cis-12-cis-15-octadecatrienoic (linolenic), eleostearic, 12-hydroxy-cis-9-octadecenoic (ricinoleic), cis-5-docosenoic, cis-5,13-docosadienoic, 12,13-epoxy-cis-9-octadecenoic (vernolic), and 14-hydroxy-cis-11-eicosenoic acid (lesquerolic) acids. The most preferred unsaturated fatty acid is oleic acid.

Generally, the fatty acid ester feedstock employed in preparing the aldehyde or alcohol compositions of this invention is obtained by transesterifying a seed oil with a lower alkanol. Transesterification produces the corresponding mixture of saturated and unsaturated fatty acid esters of the lower alkanol. Because glycerides can be difficult to process and separate, transesterification of the seed oil with a lower alkanol yields mixtures that are more suitable for chemical transformations and separation. Typically, the lower alcohol has from 1 to about 15 carbon atoms. The carbon atoms in the alcohol segment may be arranged in a straight-chain or a branched structure, and may be substituted with a variety of substituents, such as those previously disclosed hereinabove in connection with the fatty acid segment, provided that such substituents do not interfere with processing and downstream applications. Preferably, the alcohol is a straight-chain or a branched $C_{1-8}$ alkanol, more preferably, a $C_{1-4}$ alkanol. Even more preferably, the lower alkanol is selected from methanol, ethanol, and isopropanol. Most preferably, the lower alkanol is methanol.

Any known transesterification method can be suitably employed, provided that the ester products of the lower alkanol are achieved. The art adequately discloses transesterification (for example, methanolysis, ethanolysis) of seed oils; for example, refer to WO 2001/012581, DE 19908978, and BR 953081. Typically, in such processes, the lower alkanol is contacted with alkali metal, preferably sodium, at a temperature between about 30° C. and about 100° C. to prepare the corresponding metal alkoxide. Then, the seed oil is added to the alkoxide mixture, and the resulting reaction mixture is heated at a temperature between about 30° C. and about 100° C. until transesterification is effected. The crude transesterified composition may be separated from the reaction mixture by methods known in the art, including for example, phase separation, extraction, and/or distillation. The crude product may also be separated from co-products and/or decolorized using column chromatography, for example, with silica gel. Variations on the above procedure are documented in the art.

If a mixture of fatty acids, rather than fatty acid esters, is desirably employed as the feedstock for this invention, then the selected seed oil can be hydrolyzed to obtain the corresponding mixture of fatty acids. Methods for hydrolyzing seed oils to their constituent fatty acids are also well known in the art.

In the process to prepare the aldehyde composition of this invention, the mixture of fatty acids or fatty acid esters, preferably derived from a seed oil, is subjected to hydroformylation. It is preferred to employ non-aqueous hydroformylation processes that employ the operational features taught in U.S. Pat. Nos. 4,731,486 and 4,633,021, especially those taught in U.S. Pat. No. 4,731,486; the disclosures of said patents being incorporated herein by reference. Accordingly, another aspect of this invention comprises contacting the mixture of unsaturated fatty acids or fatty acid esters, preferably derived from a seed oil, with carbon monoxide and hydrogen in a non-aqueous reaction medium in the presence of a solubilized Group VIII transition metal-organophosphine metal salt ligand complex catalyst, and optionally solubilized free organophosphine metal salt ligand, under conditions sufficient to prepare the aldehyde composition described herein. The term "non-aqueous reaction medium" means that the reaction medium is essentially free of water, which means that to the extent that water is present at all, it is not present in an amount sufficient to cause the hydroformylation reaction mixture to be considered as encompassing a separate aqueous or water phase or layer in addition to the organic phase. The term "free" organophosphine metal salt ligand means that the organophosphine metal salt ligand is not complexed, that is, not bound or tied to the Group VIII transition metal.

The Group VIII transition metals are meant to be selected from the group consisting of iron (Fe), cobalt (Co), nickel (Ni), ruthenium (Ru), rhodium (Rh), palladium (Pd), osmium (Os), iridium (Ir), and platinum (Pt), and mixtures thereof; with the preferred metals being rhodium, ruthenium, cobalt, and iridium; more preferably, rhodium and cobalt; and most preferably, rhodium. The oxidation state of the Group VIII metal may be any available oxidation state, either electronically neutral (zero) or electronically deficient (positive valence), that allows for bonding to the organophosphine ligand. Moreover, the oxidation state of the Group VIII transition metal, as well as the overall oxidation state of the complex or any complex precursor, may vary under the hydroformylation process conditions. The term "complex" as used herein shall be taken to mean a coordination compound formed by the union of one or more organophosphine ligands with the Group VIII transition metal. The number of available coordination sites on the Group VIII transition metal is well known in the art and may range typically from about 4 to about 6. Optionally, the Group VIII transition metal may be additionally bonded to carbon monoxide, hydrogen, or both carbon monoxide and hydrogen. In general, the Group VIII transition metal is employed in the hydroformylation process in a concentration range of from about 10 parts per million (ppm) to about 1000 ppm, by weight, calculated as free metal. In rhodium catalyzed hydroformylation processes, it is generally preferred to employ from about 10 to about 800 ppm of rhodium calculated as free metal.

The organophosphine metal salt ligand preferably employed in the hydroformylation process of this invention comprises a monosulfonated tertiary phosphine metal salt, preferably, represented by formula I hereinafter:

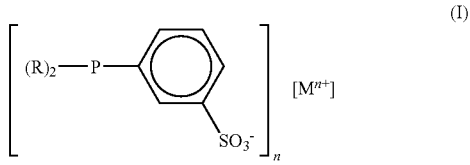

wherein each R group individually represents a radical containing from 1 to about 30 carbon atoms selected from the classes consisting of alkyl, aryl alkaryl, aralkyl, and cycloalkyl radicals; wherein M represents a metal cation selected from the group consisting of alkali and alkaline earth metals; and wherein n has a value of 1 or 2 corresponding to the valence of the particular metal cation M. Non-limiting examples of monosulfonated tertiary phosphine metal salt ligands of the aforementioned structure are illustrated in the art, for example, in U.S. Pat. No. 4,731,486, incorporated herein by reference. More preferred ligands are selected from monosulfonated metal salt derivatives of triphenylphosphine, diphenylcyclohexylphosphine, phenyldicyclohexyphosphine, tricyclohexylphosphine, diphenylisopropylphosphine, phenyldiisopropylphosphine, diphenyl-t-buylphosphine, phenyldi-t-butylphosphine, and the like. A most preferred ligand is selected from the monosulfonated metal salt derivatives of phenyldicyclohexylphosphine.

The hydroformylation process of this invention may be conducted in an excess amount of free ligand, for example, at least one mole of free monosulfonated tertiary organophosphine metal salt ligand per mole of Group VIII transition metal present in the reaction medium. In general, amounts of free ligand from about 2 to about 300, and preferably, from about 5 to about 200 moles per mole of Group VIII transition metal present in the reaction medium should be suitable for most purposes, particularly with regard to rhodium catalyzed processes. If desired, make-up organophosphine ligand can be supplied to the reaction medium or the hydroformylation process at any time and in any suitable manner, so as to maintain preferred concentrations of free ligand in the reaction medium.

The monosulfonated tertiary phosphine metal salt ligands mentioned hereinabove are generally water soluble, and not soluble or very poorly soluble in most olefins and/or aldehydes, and particularly, not soluble or very poorly soluble in the unsaturated fatty acids or fatty acid esters and formyl derivatives thereof under consideration in this invention. It is known, however, that by use of certain organic solubilizing agents, the monosulfonated tertiary phosphine metal salt ligand and Group VIII complexes thereof can be rendered organically soluble and thus employable in non-aqueous hydroformylation reaction media. Organic solubilizing agents used for the aforementioned purpose are disclosed in the prior art, for example, in U.S. Pat. No. 5,180,854 and 4,731,486, incorporated herein by reference. U.S. Pat. No. 5,180,854 discloses as organic solubilizing agents amides, glycols, sulfoxides, sulfones, and mixtures thereof. N-methyl-2-pyrrolidinone (NMP) is one preferred organic solubilizing agent. As disclosed in U.S. Pat. No. 4,731,486, other suitable polar solvents or solubilizing agents include alkylene oxide oligomers having an average molecular weight greater than about 150 up to about 10,000, and higher; organic non-ionic surfactant mono-ols having an average molecular weight of at least about 300; and alcohol alkoxylates containing both water-soluble (polar) and oil-soluble (non-polar) groups readily available under the trademark TERGITOL.

The reaction conditions for effecting the non-aqueous hydroformylation process can vary widely over conventional ranges; however, the conversion of unsaturated fatty acid(s) and/or fatty acid ester(s), as discussed hereinbelow, constitutes an important factor in providing for the compositions described herein. A reaction temperature typically greater than about 45° C., and preferably, greater than about 60° C. can be suitably employed. The hydroformylation process, however, typically operates at a temperature less than about 200° C., and preferably, less than about 130° C. Such a process generally operates at a pressure greater than about 1 psia (6.9 kPa), preferably, greater than about 50 psia (345 kPa). Typically, the process operates at a pressure less than about 10,000 psia (69 MPa), preferably, less than about 1,500 psia (10 MPa), and more preferably, less than about 500 psia (3.5 MPa). The minimum total pressure of the reactants is not particularly critical and depends predominately on the amount and nature of the reactants employed to obtain a desired rate of reaction. More specifically, the carbon monoxide partial pressure is preferably greater than about 1 psia (6.9 kPa), and more preferably, greater than about 25 psia (172 kPa). The carbon monoxide partial pressure is preferably less than about 250 psia (1,724 kPa), and more preferably, less than about 200 psia (1,379 kPa). The hydrogen partial pressure preferably is greater than about 10 psia (69 kPa), more preferably, greater than about 25 psia (172 kPa). The hydrogen partial pressure is preferably less than about 250 psia (1,724 kPa), and more preferably, less than about 200 psia (1,379 kPa). In general, the molar ratio of gaseous hydrogen to carbon monoxide ($H_2$:CO) can range from about 1:10 to about 10:1. The reaction medium residence time typically ranges from greater than about 1 hour to less than about 40 hours per reactor. The hydroformylation process can be operated as a batch process, or preferably, conducted as a continuous process with recycle of the complex catalyst and optional free ligand. A preferred reactor comprises from 1 to about 5 continuous stirred tank reactors connected in series. Each stirred tank reactor may contain one or multiple stages, as desired. Other engineering variations are known and described in the art.

As mentioned hereinabove, the conversion of unsaturated fatty acid(s) and/or fatty acid ester(s) in the hydroformylation process provides an important handle in obtaining the compositions of this invention. The conversion of unsaturated fatty acid(s) and/or fatty acid ester(s) can be conveniently measured, for example, by gas phase chromatographic (gc) methods known to those of skill in the art. More specifically, a gc peak or peaks representative of the unsaturated fatty acids or fatty acid esters (that is, compounds with no formyl substituents) are typically found to decrease in peak height and peak area as the hydroformylation progresses. The extent of this peak loss can be correlated with the conversion of unsaturated fatty acids or fatty acid esters first to monoformyl-substituted products. Some monoformyl products containing additional unsaturation will be involved in a secondary reaction to diformyl products; and some diformyl products containing additional unsaturation will be involved in a tertiary reaction to triformyl products. For the purposes of this invention, these secondary and tertiary reactions to diformyl and triformyl products are not considered in the calculation of conversion. Consideration is given only to the conversion of the first unsaturated bond per molecule of unsaturated fatty acid or fatty acid ester to monoformyl product. Under the process conditions described hereinbefore, the hydroformylation process is conducted to a conversion of greater than about 80 weight percent unsaturated fatty acids or fatty acid esters. Preferably, the conversion is greater than about 85 weight percent unsaturated fatty acids or fatty acid esters. Preferably, the conversion is less than about 99 weight percent, and more preferably, less than about 95 weight percent unsaturated fatty acids or fatty acid esters, based on the conversion of one unsaturated bond per molecule. Note that by the instant definition the conversion is not equivalent to converting greater than 80 percent of all unsaturated bonds.

When the hydroformylation process is conducted as described hereinabove, then an aldehyde composition is obtained that comprises a mixture of formyl-substituted fatty acids or fatty acid esters having the following composition by weight: from greater than about 10, preferably greater than about 25, to less than about 95 percent monoformyl, from greater than about 1 to less than about 65 percent diformyl, and from greater than about 0.1 to less than about 10 percent triformyl-substituted fatty acids or fatty acid esters; preferably, from greater than about 3 to less than about 20 percent saturates; preferably, from greater than about 1 to less than about 20 percent unsaturates; and preferably, less than about 10 percent impurities, by weight. In addition, the aldehyde composition exhibits a diformyl to triformyl weight ratio typically greater than about 5/1, preferably, greater than about 8/1, and more preferably, greater than about 10/1. Typically, the diformyl to triformyl weight ratio is less than about 250/1.

The formyl-substituted fatty acids or fatty acid esters may contain impurities including heavies. Typically, the concentration of heavies is greater than about 0.01 weight percent, but less than about 10 weight percent, based on the total weight of the aldehyde composition. Typically, the total concentration of impurities is greater than about 0.01 weight percent, based on the total weight of the aldehyde composition. Preferably, the total concentration of impurities is less than about 10, preferably, less than about 5, and more preferably, less than about 2 weight percent, based on the total weight of the aldehyde composition. Generally, it is desirable to maintain a low level of these impurities, because their presence may impact the properties of manufactured downstream end-products.

The aldehyde composition can be separated by methods known in the art from the hydroformylation reaction medium, the Group VIII transition metal-organophosphine metal salt ligand complex catalyst, and free organophosphine metal salt ligand. Extraction is a preferred method of separation. A suitable extraction method is described in U.S. Pat. No. 5,180,854, incorporated herein by reference. The extraction method disclosed therein comprises mixing the non-aqueous reaction mixture with from about 2 to about 60 percent by weight of added water and from 0 to about 60 percent by weight of a non-polar hydrocarbon, and then by phase separation forming a non-polar phase consisting essentially of the aldehyde composition and the non-polar hydrocarbon compound, if any, and a liquid polar phase consisting essentially of water, the Group VIII transition metal-organophosphine metal salt ligand complex catalyst, optionally free organophosphine metal salt ligand, and any organic solubilizing agent. Typically, the non-polar hydrocarbon comprises a saturated straight chain alkane containing from about 6 to about 30 carbon atoms, such as, hexane. The aldehyde composition may be processed directly in the non-polar hydrocarbon, or of desired, may be separated by conventional methods from the non-polar hydrocarbon. The hydroformylation complex catalyst and organophosphine ligand are typically extracted from the liquid polar phase and recycled back to the hydroformylation reactor. As a result of the above-described hydroformylation and separation procedures, the aldehyde composition may additionally comprise small quantities of water, hydroformylation solvent, solubilizing agent, and/or extraction solvent.

The conversion of aldehydes to alcohols is known in the art, and such conventional methods can be applied to convert the aldehyde composition of this invention to the alcohol composition of this invention. Typically, the aldehyde composition comprising the mixture of formyl-substituted fatty acids or fatty acid esters is contacted with a source of hydrogen in the presence of a hydrogenation catalyst under hydrogenation process conditions sufficient to prepare the alcohol composition of hydroxymethyl-substituted fatty acids or fatty acid esters. The source of hydrogen may be pure hydrogen or hydrogen diluted with a non-reactive gas, such as nitrogen, helium, argon, a saturated hydrocarbon, or the like. The hydrogenation catalyst may be any such catalyst capable of converting the aldehyde composition to the alcohol composition. Preferably, the hydrogenation catalyst comprises a metal selected from Group VIII, Group IB, and Group IIB of the Periodic Table, and mixtures thereof; more preferably, a metal selected from palladium, platinum, rhodium, nickel, copper, and zinc, and mixtures thereof. The metal may be supplied as Raney metal or as supported metal on a suitable catalyst support, such as carbon or silica. An even more preferred hydrogenation catalyst is Raney nickel or supported nickel. The hydrogenation may be conducted neat or in a solution of a suitable hydrocarbon solvent. The temperature for such hydrogenations is generally greater than about 50° C., and preferably, greater than about 80° C. The temperature for such hydrogenations is typically less than about 250° C., and preferably, less than about 175° C. The hydrogen pressure is generally greater than about 50 psig (345 kPa). The hydrogen pressure is generally less than about 1,000 psig (6,895 kPa), and preferably, less than about 600 psig (4,137 kPa).

The hydrogenation conducted as described hereinabove produces the alcohol composition comprising a mixture of hydroxymethyl-substituted fatty acids or fatty acid esters comprising in terms of hydroxy distribution from greater than about 10, preferably greater than about 25, to less than about 95 percent monoalcohol, from greater than about 1 to less than about 65 percent diol, and from greater than about 0.1 to less than about 10 percent triol; preferably, from greater than about 3 to less than about 35 percent saturates; and preferably, from greater than about 0 to less than about 10 percent unsaturates. The alcohol composition is further characterized as preferably comprising a diol to triol weight ratio of greater than about 2.5/1, more preferably, greater than about 5/1, even more preferably, greater than about 8/1, and most preferably, greater than about 10/1. Generally, the diol to triol weight ratio is less than about 250/1.

The alcohol composition may contain impurities, such as lactols, lactones, saturated and unsaturated cyclic ethers, and heavies, for example, having the structures shown in FIG. 1 for a fatty acid of carbon chain length 18. Analogous species may be present based on fatty acids or fatty acid esters having different substitution or having chain lengths different from 18. Typically, the concentration of lactols and/or lactones is greater than about 0.01 weight percent, based on the total weight of the alcohol composition. Typically, the concentration of lactols and/or lactones is less than about 20, and preferably, less than about 10 weight percent, based on the total weight of the alcohol composition. Typically, the concentration of unsaturated and/or saturated cyclic ethers is greater than about 0.01 weight percent, based on the total weight of the alcohol composition. Typically, the concentration of unsaturated and/or saturated cyclic ethers is less than about 10 weight percent, based on the total weight of the alcohol composition. Typically, the concentration of heavies is greater than about 0.01 weight percent, based on the total weight of the alcohol composition. Typically, the concentration of heavies is less than about 10 weight percent, based on the total weight of the alcohol composition. Typically, the total concentration of impurities is greater than about 0.01 weight percent, based on the total weight of the alcohol composition. Preferably, the total concentration of impurities is less than about 10, preferably, less than about 5, and more preferably, less than about 2 weight percent, based on the total weight of the alcohol composition. Generally, it is desirable to maintain a low level of these impurities, because their presence may impact the properties of manufactured downstream end-products.

The alcohol composition disclosed herein may be oligomerized in the presence of a catalytic initiator to form oligomeric polyol compositions that find utility in the preparation of polyurethane slab stock flexible foam applications. Representative process conditions for the alcohol oligomerization and description of the polyols derived therefrom may be found in U.S. Provisional Patent Application Ser. No. 60/465,685, entitled "IMPROVED PROCESS TO MAKE VEGETABLE OIL BASED POLYOLS AND POLYOLS MADE THEREFROM," filed Apr. 25, 2003, in the names of Zenon Lysenko et al.; and in related U.S. Pat. No. 7,960,444, entitled "VEGETABLE OIL BASED POLYOLS AND POLYOLS MADE THEREFROM," in the names of Zenon Lysenko et al., which non-provisional application claims the priority benefit of said Provisional Patent Application Ser. No. 60/465,685; said provisional and non-provisional patent applications being incorporated herein by reference. The oligomeric polyol compositions thus prepared generally possess an average molecular weight in the range from about 600 to about 6,000. Polyurethanes prepared with these oligomeric polyols possess acceptable properties, including acceptable cross-link density, for use in slab stock flexible foams. Details of the manufacture of such foams and description of their properties may also be found in the aforementioned co-pending U.S. patent application.

The following examples are presented hereinbelow to illustrate the inventions described herein. The examples should not be construed to limit the inventions in any manner.

Based on the description provided herein, variations and modifications of the examples will be apparent to those of skill in the art.

General Method of Analyzing Aldehyde Composition

Samples were analyzed after addition of an internal standard (diglyme). Analysis was made by gas chromatography (GC) using a HP 6890 gas chromatograph with a DB-5 capillary column. A flame ionization detector (FID) was used, and calibration was made by the internal standard method. Response factors for the following components were obtained by direct calibration: methyl palmitate, methyl stearate, methyl oleate, methyl linoleate, and methyl formylstearate. Response factors for the remainder of the target components were obtained by analogy. Conversion, calculated as percent conversion, was determined by the disappearance of the sum of the methyl oleate, methyl linoleate, and methyl linolenate peaks.

General Method of Analyzing Alcohol Composition

The alcohol composition was analyzed after dilution (dioxane) and addition of an internal standard (diglyme). Analysis was by GC using a HP 5890 gas chromatograph with a DB-5 capillary column. Detection was by FID, and calibration was made by the internal standard method. Response factors for the following components were obtained by direct calibration: methyl palmitate, methyl stearate, methyl formylstearate, and methyl hydroxymethylstearate. Response factors for the remainder of the target components were obtained by analogy. Conversion, calculated as percent conversion, was determined by the disappearance of the methyl formylstearate peak.

General Method of Analyzing for Dimers and Heavies Impurities in Aldehyde and Alcohol Compositions Samples were analyzed after dilution in dioxane. Analysis was by GC using a HP 6890 gas chromatograph and a ZB-1 capillary column run at 100-350° C. Detection was by FID; and the analysis used a "Normalized Area Percent" method after splitting the chromatogram into two regions: a products region and a heavies region.

EXAMPLE 1

A catalyst solution was prepared by dissolving dicarbonylacetylacetonato rhodium (I) (0.078 g) and dicyclohexyl-(3-sulfonoylphenyl)phosphine mono-sodium salt (0.7513 g) in n-methyl-2-pyrrolidinone (NMP) (53.8934 g) under a nitrogen atmosphere. A portion of the resulting mixture (11.06 g) was then transferred to a nitrogen-purged 100 mL stainless steel autoclave and heated to 90° C. under 200 psig (1,379 kPa) of synthesis gas (1:1 hydrogen:carbon monoxide) with mixing via mechanical agitation at 700 rpm. The mixture was heated for about 15 minutes. To this mixture was added under synthesis gas soy methyl esters (38.98 g) comprising by weight 9 percent methyl palmitate, 5 percent methyl stearate, 24 percent methyl oleate, 51 percent methyl linoleate, and 8 percent methyl linolenate. The reactor pressure was maintained at 400 psig (2,758 kPa) by the addition of fresh synthesis gas. The mixture was analyzed after 22.5 hours of reaction time. The resulting unsaturated ester conversion and aldehyde composition are shown below in Table 1.

TABLE 1

Aldehyde Compositions Derived from Hydroformylation of Soy Methyl Esters

| Ex. | % Conv | Saturates | Unsats | Monoformyl | Diformyl | Triformyl | Heavies | Di/Tri Ratio |
|---|---|---|---|---|---|---|---|---|
| 1 | 84 | 14 | 14 | 40 | 30 | 2 | 0.2 | 15/1 |
| 2 | 88 | 14 | 10 | 37 | 37 | 2 | 1.3 | 18/1 |
| 3 | 98 | 14 | 2 | 33 | 48 | 4 | 0.3 | 12/1 |
| 4 | 95 | 14 | 4 | 34 | 44 | 4 | 0.5 | 11/1 |

EXAMPLE 2

The procedure described in Example 1 was repeated with the following modifications: catalyst solution (10.92 g) and soy methyl esters (39.19 g). Temperature was maintained at 90° C. and pressure at 400 psig (2,758 kPa). After 20 hours of reaction time an aldehyde composition obtained from the reaction mixture was analyzed with the results shown in Table 1.

EXAMPLE 3

A catalyst solution was prepared by dissolving dicarbonylacetylacetonato rhodium (I) (0.080 g) and dicyclohexyl-(3-sulfonoylphenyl)phosphine mono-sodium salt (0.3514 g) in n-methyl-2-pyrrolidinone (NMP) (54.059 g) under a nitrogen atmosphere. A portion of the resulting mixture (11.17 g) was then transferred to a nitrogen-purged 100 mL stainless steel autoclave and heated to 90° C. under 200 psig (1,379 kPa) of synthesis gas (1:1 hydrogen:carbon monoxide) with mixing via mechanical agitation at 700 rpm. The mixture was heated for about 15 minutes. To this mixture was added under synthesis gas soy methyl esters (39.09 g) comprising by weight 9 percent methyl palmitate, 5 percent methyl stearate, 24 percent methyl oleate, 51 percent methyl linoleate, and 8 percent methyl linolenate. The reactor pressure was maintained at 400 psig (2,758 kPa) by the addition of fresh synthesis gas. The mixture was analyzed after 25.5 hours of reaction time. The resulting unsaturated ester conversion and aldehyde composition are shown in Table 1.

EXAMPLE 4

The procedure described in Example 3 was repeated with the following modifications. The catalyst solution (11.08 g) and soy methyl ester (38.49 g) were transferred to the reactor where the temperature was maintained at 70° C. and the pressure at 400 psig for 20 hours. The resulting unsaturated ester conversion and aldehyde composition are shown in Table 1.

EXAMPLE 5

An up-flow tubular reactor was packed with a commercial supported nickel catalyst (440 mL, Sud-Chemie C46-8-03). The inlet of the reactor was comprised of two liquid feeds and one gas feed that came together before entering the reactor. The two liquid feeds consisted of a hydroformylated soy methyl ester (saturates 13 percent, mono-aldehyde 34.3 percent, dialdehyde 45.1 percent, trialdehyde 1.5 percent) and recycled hydrogenation product from the same aldehyde supply. The flow rate of the hydroformylated soy methyl ester was 5 g/min; the flow rate of the recycled hydrogenation product was 19 g/min. Total Liquid Hourly Space Velocity was 3.51 hr$^{-1}$. Hydrogen gas was fed to the reactor at 2,000 sccm (Gas Hourly Space Velocity 272 hr$^{-1}$), and the reactor was heated to 143° C. Pressure was set at 830 psig (5,723 kPa). Analysis of the mixture after hydrogenation yielded the alcohol composition described in Table 2.

TABLE 2

Alcohol Compositions Derived from Hydrogenation of Formyl-Substituted Fatty Acid Esters[1,2]

| Example | Saturates | Monool | Diol | Triol | Dimer Heavies | Lactones | Ethers |
|---|---|---|---|---|---|---|---|
| 5 | 18.8 | 34.7 | 37.8 | 3.2 | 2.5 | 0.2 | 0.32 |
| 6 | 23.8 | 35.0 | 34.7 | 2.3 | 1.6 | 0.6 | nd |
| 7 | 30.6 | 38.2 | 25.3 | 1.3 | 2.6 | 0.5 | 0.1 |

[1]Nd = Not detected.
[2]Unsaturates not detected in any of Examples 5 to 7.

EXAMPLE 6

Hydrogenation was conducted on a formylated feed using the reactor design and catalyst described in Example 5. The two liquid feeds consisted of a hydroformylated soy methyl ester (saturates 13.8 percent, mono-aldehyde 35.4 percent, dialdehyde 39.8 percent, trialdehyde 0.6 percent) and recycled hydrogenation product from the same aldehyde supply. The flow rate of the hydroformylation soy methyl ester was 2 g/min; the flow rate of the recycled hydrogenation product was 8 g/min Total Liquid Hourly Space Velocity was 5.5 hr$^{-1}$. Hydrogen gas was fed at 1,000 sccm (Gas Hourly Space Velocity 471 hr$^{-1}$. The reactor was heated to 163° C. and maintained at 590 psig (4,068 kPa). Analysis of the mixture after hydrogenation yielded the alcohol composition described in Table 2.

EXAMPLE 7

Hydrogenation was conducted on a formylated feed using the reactor design and catalyst described in Example 5. The two liquid feeds consisted of hydroformylated soy methyl ester (saturates 14.2 percent, mono-aldehyde 43 percent, dialdehyde 30.6 percent, trialdehyde 0.4 percent) and recycled hydrogenation product from the same aldehyde supply. The flow rate of the hydroformylated soy methyl ester was 1.89 g/min; the flow rate of the recycled hydrogenation product was 8.2 g/min Total Liquid Hourly Space Velocity was 5.14 hr$^{-1}$). Hydrogen gas was fed at 1,000 sccm (Gas Hourly Space Velocity 471 hr$^{-1}$ and the reactor was heated to 161° C. Pressure was set at 610 psig (4,206 kPa). Analysis of the mixture after hydrogenation yielded the alcohol composition described in Table 2.

EXAMPLE 8

In a stainless steel reactor, a solution was prepared containing rhodium (120 parts per million by weight (ppmw)) in the form of dicarbonylacetylacetonato rhodium (I), dicyclohexyl-(3-sulfonoylphenyl)phosphine mono-sodium salt (0.3 percent), 1-methyl-2-pyrrolidinone (NMP) (21.6 percent), and soy derived methyl esters (78.1 percent), all percentages by weight. The soy derived methyl esters consisted of 84 percent olefins and 15 percent saturates, by weight. The mixture was placed under 400 psig (2,758 kPa) of synthesis gas (1:1 hydrogen:carbon monoxide) at room temperature, slowly warmed to 90° C., and then maintained at a constant 90° C. temperature. During heating the pressure of the system reached a maximum of 450 psig (3,103 kPa). The pressure was maintained at 400 psig (2,758 kPa) throughout the reaction by the addition of fresh synthesis gas, aside from the pressure increase observed during the initial heating. After reacting for 11 hours, the mixture was sampled for analysis. The mixture was cooled to ambient temperature, nitrogen sparged for about 1 hour, then discharged from the reactor into a container under a nitrogen atmosphere at atmospheric pressure. An aldehyde composition was obtained having the composition shown in Table 3, calculated on the basis of the olefin charged to the system.

TABLE 3

| Ex. | % Conv | % Sats | % Unsats | % Monoformyl | % Diformyl | % Triformyl | Heavies | Di/Tri Ratio |
| --- | --- | --- | --- | --- | --- | --- | --- | --- |
| 8 | 98 | 14 | 2 | 31 | 49 | 5 | 0.5 | 9.8 |
| 9 | 93 | 14 | 6 | 35 | 41 | 4 | 0.2 | 10.3 |
| 10 | 92 | 14 | 7 | 34 | 41 | 4 | 0.2 | 10.3 |
| 11 | 92 | 14 | 6 | 34 | 41 | 4 | 0.2 | 10.3 |
| 12 | 92 | 14 | 6 | 34 | 42 | 4 | 0.4 | 10.5 |

EXAMPLES 9-11

The procedure of Example 8 was repeated three times as Examples 9, 10, and 11, with the modification of a reaction time of 5.5 hours. Aldehyde compositions were obtained, as shown in Table 3.

EXAMPLE 12

The procedure of Example 8 was repeated with the modification of a reaction time of 6 hours. An aldehyde composition was obtained, as shown in Table 3.

EXAMPLE 13

The aldehyde compositions obtained from Examples 9, 10, and 11 were combined, mixed with water at 70° C. (water was 60 percent by weight of the total organic mass). The mixture was allowed to settle and the organic layer separated from the aqueous layer. The organic layer was washed four additional times with water, in each instance the water layer was removed from the organic layer after allowing the phases to separate. Analysis of the organic layer after washing showed that 98 percent of the rhodium and greater than 99 percent of the NMP had been removed from the organic layer. The composition of the organic layer is shown below in Table 4.

TABLE 4

| Component | Composition (% by wt) |
| --- | --- |
| Saturates + Olefins | 20 |
| Monoaldehyde | 34 |
| Dialdehyde | 40 |

TABLE 4-continued

| Component | Composition (% by wt) |
| --- | --- |
| Trialdehyde | 4 |
| Heavies | 0.3 |
| NMP | 0.1 |
| Di/Tri Ratio | 10/1 |

The hydroformylated soy methyl ester composition (50 g), obtained from the above extraction, and Raney® Nickel 2400 (1.5 g, Grace Davison) were charged into a pressure reactor under air and the reactor was sealed. Nitrogen (100 psig, 689 kPa) was slowly pressurized into the reactor and then released slowly. This was repeated three times to replace the air in the reactor with nitrogen. The reactor was purged hydrogen. The reactor was then stirred at 844 rpm with mechanical agitation, and heated to 120° C. under 400 psig (2,758 kPa) of hydrogen. The reactor was then fed with hydrogen to maintain reaction pressure at 400 psig (2,758 kPa). Analysis of the mixture after 24.1 hours of reaction time yielded the alcohol composition described in Table 5.

TABLE 5

| Component | Alcohol Composition (Wt. %) |
| --- | --- |
| Saturates + Olefins | 19 |
| Monoalcohol | 34 |
| Diol | 40 |
| Triol | 4 |
| Heavies | 1.2 |
| Lactones | 0.5 |
| Ethers | Nd[1] |

[1]ND = Not detected.

EXAMPLE 14

A catalyst solution was prepared by dissolving dicarbonylacetylacetonato rhodium (I) (0.063 g) and dicyclohexyl-(3-sulfonoylphenyl)phosphine mono-sodium salt (1.10 g) in n-methyl-2-pyrrolidinone (NMP) (16.0 g) under a nitrogen atmosphere. The resulting mixture was then transferred to a nitrogen-purged 100 mL stainless steel autoclave and heated to 75° C. under 200 psig (1,379 kPa) of synthesis gas (1:1 hydrogen:carbon monoxide) with mixing via mechanical agitation at 700 revolutions per minute (rpm). The mixture was heated for about 15 minutes. To this mixture was added under synthesis gas soy methyl esters (34.05 g) comprising by weight 9 percent methyl palmitate, 5 percent methyl stearate, 25 percent methyl oleate, 52 percent methyl linoleate, and 8 percent methyl linolenate. The reactor pressure was maintained at 400 psig (2,758 kPa) by the addition of fresh synthesis gas. The mixture was analyzed after 3 hours of reaction time. The resulting unsaturated ester conversion and aldehyde composition are shown in Table 6.

TABLE 6

| Ex. | % Conv. | Sats | Unsats | Mono-formyl | Di-formyl | Tri-formyl | Heavies | Di/Tri Ratio |
|---|---|---|---|---|---|---|---|---|
| 14 | 91 | 14 | 7 | 39 | 38 | 2 | Nd | 17 |

EXAMPLE 15

An up-flow tubular reactor was packed with a commercial supported nickel catalyst C46-8-03 (355 mL of catalyst) from Sud-Chemie. The inlet of the reactor was comprised of two liquid feeds and one gas feed that came together before entering the reactor. The two liquid feeds consisted of 3.52 g/min hydroformylated soy methyl ester (saturates 13.7 percent, mono-aldehyde 36.9 percent, dialdehyde 34.1 percent, trialdehyde 2.1 percent) and 16.5 g/min recycled hydrogenation product from the same aldehyde supply (total Liquid Hourly Space Velocity 3.65 hr$^{-1}$). Hydrogen gas was fed at 2,000 standard cubic centimeters per minute (sccm) (Gas Hourly Space Velocity 338 hr$^{-1}$). The reactor tube was heated to 159° C., and the reactor outlet pressure was 459 psig (31,65 kPa). Analysis of the mixture after hydrogenation yielded the alcohol composition shown in Table 7.

TABLE 7

Alcohol Composition[1]

| Ex. | Sats | Mono-alcohol | Di-alcohol | Tri-alcohol | Heavies | Lactones | Ethers |
|---|---|---|---|---|---|---|---|
| 15 | 22.1 | 37.4 | 31.3 | 2.3 | 1.4 | 0.7 | 0.6 |

[1]In the gc region for unsaturates, the total of several small peaks is 1.5 percent.

EXAMPLE 16

An up-flow tubular reactor was packed with a commercial supported nickel catalyst C46-8-03 (355 mL of catalyst) from Sud-Chemie. The inlet of the reactor was comprised of two liquid feeds and one gas feed that came together before entering the reactor. The two liquid feeds consisted of 3.25 g/min hydroformylated canola methyl ester (saturates 11.1 percent, mono-aldehyde 55.3 percent, dialdehyde 15.9 percent, trialdehyde 4.5 percent) and 13.87 g/min recycled hydrogenation product from the same aldehyde supply (total Liquid Hourly Space Velocity 3.13 hr$^{-1}$). Hydrogen gas was fed at 2,000 sccm (Gas Hourly Space Velocity 338 hr$^{-1}$). The tube was heated to 157° C., and the reactor outlet pressure was 475 psig (3,275 kPa). Analysis of the mixture after hydrogenation yielded the alcohol composition shown in Table 8.

TABLE 8

Alcohol Composition[1]

| Ex. | Sats | Mono-alcohol | Di-alcohol | Tri-alcohol | Heavies | Lactones | Ethers |
|---|---|---|---|---|---|---|---|
| 16 | 20.6 | 53.6 | 14.6 | 5.5 | 2.3 | 0.6 | 0.6 |

[1]In the gc region for unsaturates, the total of several small peaks is 0.25 percent.

What is claimed is:

1. An aldehyde composition comprising a mixture of formyl-substituted fatty acids or fatty acid esters comprising in terms of formyl distribution from greater than about 10 to less than about 95 percent monoformyl, from greater than about 1 to less than about 65 percent diformyl, and from greater than about 0.1 to less than about 10 percent triformyl by weight, based on the total weight of the composition, and further comprising a diformyl to triformyl weight ratio of greater than about 5/1.

2. The aldehyde composition of claim 1 further comprising from greater than about 3 to less than about 20 percent saturates, by weight.

3. The aldehyde composition of claim 1 or 2 further comprising from greater than about 1 to less than about 20 percent unsaturates, by weight.

4. The aldehyde composition of claim 1 wherein the diformyl to triformyl weight ratio is greater than about 10/1.

5. The aldehyde composition of claim 1 comprising less than about 10 weight percent total heavies impurities.

6. The aldehyde composition of claim 1 comprising from greater than about 25 to less than about 45 percent monoformyl, from greater than about 20 to less than about 50 percent diformyl, and from greater than about 0.5 to less than about 5 percent triformyl substituted fatty acids or fatty acid esters, by weight.

7. The aldehyde composition of claim 1 comprising from greater than about 30 to less than about 40 percent monoformyl, from greater than about 25 to less than about 45 percent diformyl, and from greater than about 1 to less than about 2.6 percent triformyl substituted fatty acids or fatty acid esters, by weight.

8. The aldehyde composition of claim 1 being prepared by a process comprising contacting a mixture of unsaturated fatty acids or unsaturated fatty acid esters with carbon monoxide and hydrogen in the presence of a Group VIII transition metal-organophosphine metal salt ligand complex catalyst, and optionally free organophosphine metal salt ligand, under process conditions sufficient to convert greater than about 80 and less than 99 weight percent of unsaturated fatty acids or fatty unsaturated acid esters to monoformyl products, based upon the conversion of one unsaturated bond per molecule of unsaturated fatty acid or unsaturated fatty acid ester.

9. The composition of claim 8 wherein the mixture of unsaturated fatty acids or fatty acid esters is derived from a seed oil.

10. The composition of claim 8 wherein the seed oil is selected from naturally occurring and genetically modified seed oils of the group consisting of castor, soybean, olive, peanut, rapeseed, corn, sesame, cottonseed, canola, safflower, linseed, sunflower, including high oleic oils, and mixtures thereof.

11. The composition of claim 8 wherein the temperature is greater than about 45° C. and less than about 200° C., and wherein the total pressure is greater than about 1 psia (6.9 kPa) and less than about 10,000 psia (69 MPa).

12. A process of preparing an aldehyde composition comprising contacting a mixture of unsaturated fatty acids or unsaturated fatty acid esters with carbon monoxide and hydrogen in the presence of a Group VIII transition metal-organophosphine metal salt ligand complex catalyst, and optionally free organophosphine metal salt ligand, under process conditions sufficient to hydroformylate greater than about 80 and less than 99 weight percent of the unsaturated fatty acids or unsaturated fatty acid esters to monoformyl products, based upon the conversion of one unsaturated bond per molecule of unsaturated fatty acid or unsaturated fatty acid ester, so as to produce a mixture of formyl-substituted fatty acids or fatty acid esters comprising in terms of formyl distribution from greater than about 10 to less than about 95 percent monoformyl, from greater than about 1 to less than about 65 percent diformyl, and from greater than about 0.1 to less than 10 percent triformyl by weight, based on the total weight of the composition, and having a diformyl to triformyl weight ratio of greater than about 5/1.

13. The process of claim 12 wherein the ligand is a monosulfonated tertiary organophosphine represented by the following formula:

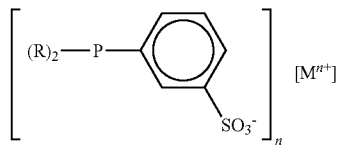

wherein each R group individually represents a radical containing from 1 to about 30 carbon atoms; wherein M represents a metal cation selected from the group consisting of alkali and alkaline earth metals; and wherein n has a value of 1 or 2 corresponding to the valence of the particular metal cation M.

14. The process of claim 13 wherein the ligand is selected from the group consisting of the monosulfonated metal salts of triphenylphosphine, diphenylcyclohexylphosphine, phenyldicyclohexylphosphine, tricyclohexylphosphine, diphenylisopropylphosphine, phenyldiisopropylphosphine, diphenyl-t-buylphosphine, phenyldi-t-butylphosphine, and mixtures thereof.

15. The process of claim 12 wherein the Group VIII transition metal of the complex catalyst is selected from rhodium, ruthenium, cobalt, iridium, and mixtures thereof.

16. The process of claim 12 wherein the temperature is greater than about 45° C. and less than about 200° C., and wherein the total pressure is greater than about 1 psia (6.9 kPa) and less than about 10,000 psia (69 MPa).

17. The process of claim 12 wherein the carbon monoxide partial pressure is greater than about 1 psia and less than about 250 psia; and wherein the hydrogen partial pressure is greater than about 10 psia and less than about 250 psia.

* * * * *